United States Patent [19]

Ulin et al.

[11] 4,373,629
[45] Feb. 15, 1983

[54] USED SURGICAL SHARPS CONTAINER WITH RE-USABLE MAGNETIC BASE

[75] Inventors: Roy A. Ulin, Wyckoff; Ted Foley, West Milford, both of N.J.; Hasmukh Shah, Bombay, India

[73] Assignee: Akzona Incorporated, Asheville, N.C.

[21] Appl. No.: 271,873

[22] Filed: Jun. 9, 1981

[51] Int. Cl.³ .............................................. A45C 11/26
[52] U.S. Cl. ..................................... 206/350; 206/570; 206/818
[58] Field of Search ............... 206/363, 438, 350, 508, 206/1.7, 119, 340, 341, 347, 370, 380, 382, 477, 558, 594, 818, 828; 128/1.3, 1.4, 272; 269/8

[56] References Cited

U.S. PATENT DOCUMENTS

| | | |
|---|---|---|
| 59,095 | 10/1866 | Totten . |
| 300,441 | 6/1884 | Borst . |
| 963,454 | 7/1910 | Meinecke . |
| 1,231,674 | 7/1917 | Underwood . |
| 1,436,617 | 11/1922 | Warren et al. . |
| 1,654,554 | 1/1928 | Pasch . |
| 1,835,408 | 12/1931 | Kurtz, Jr. . |
| 1,980,141 | 11/1934 | MacGregor ..................... 206/43 |
| 2,176,452 | 10/1939 | Choffel ........................... 206/63.3 |
| 2,583,043 | 1/1952 | Dean ............................... 206/63.3 |
| 2,588,589 | 3/1952 | Tauber ............................ 223/109 |
| 2,677,394 | 5/1954 | Brinen et al. ................... 138/38 |
| 2,692,676 | 10/1954 | Grover ............................ 206/63.3 |
| 2,888,136 | 5/1959 | La Borde ........................ 206/66 |
| 3,056,525 | 10/1962 | Deinert ........................... 220/356 |
| 3,388,790 | 6/1968 | Slomczewski ................. 206/63.3 |
| 3,481,462 | 12/1969 | Chapel ............................ 206/63.2 |
| 3,565,281 | 2/1971 | Collie ............................. 220/69 |
| 3,697,223 | 10/1972 | Kovalcik et al. .............. 21/83 |
| 3,727,658 | 4/1973 | Eldridge, Jr. .................. 150/52 R |
| 3,814,277 | 6/1974 | La Croce et al. ............. 220/356 |
| 3,819,039 | 6/1974 | Erickson ........................ 206/388 |
| 3,861,521 | 1/1975 | Burtz .............................. 206/63.3 |
| 3,868,016 | 2/1975 | Szpur et al. .................... 206/350 |
| 3,944,069 | 3/1976 | Eldridge, Jr. .................. 206/350 |
| 3,982,631 | 9/1976 | Kunik et al. .................... 206/380 |
| 4,008,802 | 2/1977 | Freitag ............................ 206/63.3 |
| 4,013,109 | 3/1977 | Sandel ............................. 150/52 R |
| 4,076,882 | 2/1978 | Fenster et al. ................. 428/215 |
| 4,105,115 | 8/1978 | Horvath et al. ................ 206/370 |
| 4,116,333 | 9/1978 | Pavel .............................. 206/380 |
| 4,182,448 | 1/1980 | Huck et al. ..................... 206/380 |
| 4,193,496 | 3/1980 | Barratt ............................ 306/380 |
| 4,243,140 | 1/1981 | Thurn ............................. 206/380 |

FOREIGN PATENT DOCUMENTS

| | | |
|---|---|---|
| 132127 | 3/1933 | Austria . |
| 2138624 | 2/1973 | Fed. Rep. of Germany ...... 206/350 |
| 2507976 | 9/1976 | Fed. Rep. of Germany . |
| 2601512 | 3/1977 | Fed. Rep. of Germany . |
| 2609288 | 9/1977 | Fed. Rep. of Germany . |
| 2651315 | 3/1978 | Fed. Rep. of Germany . |
| 2657627 | 6/1978 | Fed. Rep. of Germany . |
| 2740335 | 3/1979 | Fed. Rep. of Germany . |
| 2800579 | 7/1979 | Fed. Rep. of Germany . |
| 2836962 | 3/1980 | Fed. Rep. of Germany . |
| 1346460 | 11/1958 | France . |
| 1216548 | 7/1928 | United Kingdom . |
| 1448543 | 2/1974 | United Kingdom . |
| 1514390 | 11/1976 | United Kingdom . |
| 365203 | 6/1973 | U.S.S.R. . |

OTHER PUBLICATIONS

Floriano Papi et al., "Orientation of Anosmatic Pigeons", J. Comp. Physiol. 135 at 227-232, (1980).
Von Günther Becker, "Einfluss Örtlicher Geomagnetischer und Anderer Physikalischer Bendingungen in einem Versuchsraum auf Verschiedene Insekten", Z. Angew Zool. 66 (4) at 391-416, (1979).

Primary Examiner—Joseph Man-Fu Moy
Assistant Examiner—David Fidei
Attorney, Agent, or Firm—Robert H. Falk; Charles A. Wendel; Francis W. Young

[57] ABSTRACT

A new and useful container is disclosed for storing "sharps", e.g., surgical needles or blades, comprising: (a) base means formed of a reusable and sterilizable material containing a source of magnetism; (b) collecting means for surgical needles or blades, said collecting means shaped to provide an interlocking fit with said base means; and (c) cover means with said collecting means to form an enclosure, said cover means capable of tight-fitting engagement with and placement over said collecting means to prevent said surgical needles or blades from escaping from said enclosure when said cover means is in tight-fitting engagement with said collecting means, said collecting means and said cover means attached to each other by hinge means, said collecting means being provided with locking means to lock said cover means with said collecting means when said cover means is in tight fitting engagement with said collecting means. Preferably, the base comprises two or more parallel magnetized ribs mounted on and protruding from a platform, which exist in tight-fitting engagement with conforming apertures in the collecting means, which ribs and apertures synergistically (1) provide a source of magnetism just adequate to attract all sharps when placed into the container and (2) secure the sharps between the collecting means and cover means when the locking means is locked.

22 Claims, 19 Drawing Figures

USED SURGICAL SHARPS CONTAINER WITH RE-USABLE MAGNETIC BASE

BACKGROUND TO THE INVENTION

1. Field of the Invention

The present invention relates to the field of receiving and counting instruments for surgical "sharps", i.e., surgical needles and blades and other small surgical implements capable of being magnetically attracted prior to their disposal. More specifically, the invention relates to the field of manufacture of containers used to receive these instruments during an operation and which provide a systematic means for counting the implements after use and/or as they are removed from the body of the patient. Finally, the present invention provides an inexpensive means of disposing of the sharps after the operation is completed.

2. Description of the Prior Art and Other Information

During virtually every surgical procedure, sharp implements ("sharps"), such as surgical ["suture"] needles and ["scalpel"] blades and hypodermic needles are utilized, and, following the surgical procedure, must be counted and discarded in a safe manner. First, surgical practice has long recognized the danger of the possibility that small surgical instruments may be left within the body of a patient during surgical procedures. Even the most acute visual inspection of the patient may not reveal the presence of some types of small surgical implements which are left in the patient's body, and, therefore, an accounting system is often used. The number of implements available to the surgeon are counted prior to the operation and again counted as they are removed from the patient's body. The lack of an implement at the end of the operation indicates that it has been misplaced and possibly inadvertently left within the patient's body, and an exhaustive search of the operating room and patient, including the incision, must be performed until the implement is found. If necessary, an X-ray search of the patient is performed.

Although the implements may be routinely counted before the operation, during the closure of the incision the count must be made with great rapidity so as not to extend materially the amount of time that the patient is under surgery. Moreover, if the counting and disposal aspects of the sharps are ignored, injury to and infection of the patient may occur. This process of counting the implements can be facilitated by devices which are used to retain the blades, surgical needles, staples, and other small instruments and implements as they are used and/or removed from the patient, as the case may be. Such devices are best represented by FIGS. 1-6 hereto and the descriptions in U.S. Pat. Nos. 4,243,140 to Thrun; 4,193,496 to Barratt; 4,167,230 to Barratt; 4,013,109 to Sandel; 3,944,069 to Eldridge; 3,861,521 to Burtz; and 3,727,658 to Eldridge. To perhaps a somewhat lesser extent the devices described in U.S. Pat. Nos. 4,182,448 to Huck et al.; 4,116,333 to Pavel; 4,105,115 to Horvath et al.; 4,076,882 to Fenster et al.; 4,008,802 to Freitag; 3,819,039 to Erickson; and 3,697,223 to Kovalcik et al. are also pertinent. While these relatively expensive devices have been partially successful in the counting and disposal of sharps, they have virtually ignored a competing problem—the accelerating cost of hospital disposables, which have, no doubt, added to the total rate of inflation of hospital costs—including physician fees, hospital supplies, laboratory costs and room and board—which rate of inflation, over a decade, has been roughly double that of the general economy.

As seen below, various prior art and state of the art devices have been designed to aid nursing personnel in counting sharps. One of the more popular versions consists of a rubber pad to which a series of magnets are attached. The used needles and blades are held in place by the magnets, thus facilitating count. Upon conclusion of the operating procedure, the magnets, rubber pad, and the used blades are discarded.

U.S. Pat. No. 4,243,140 to Thrun is representative of the state of the art in disposable sharps containing devices in which no magnet is utilized; while the device provides an excellent means of counting devices, the necessity of having to place sharps such as needles 46 or 44 into slots 60 or in resilient material 38 is time-consuming; moreover, the device is lightweight and can be easily jarred which would risk loss of the contents in the surrounding environment with more loss of time to find all the instruments.

U.S. Pat. No. 4,193,496 to Barratt (see FIG. 6 attached hereto) also represents a state of the art device using a system of a disposable advanced bottom tray and top cover that, when closed and in a nested configuration, are capable of securely encasing sharps therebetween. See col. 2, lines 26-64. The description at col. 5, lines 48-62 discloses a resilient material 34 which "may be an array of magnetic strips, or the like . . . the material 34 may be coated with a layer of adhesive, or an array of magnetic strips, or the like . . . the material 34 may be formed with a series of raised ridges through which needles and sutures, etc., may be passed for retention". Any possible use of magnets in Barratt 4,193,496 are, therefore, to be employed in the disposable device, which would again provide a safer means of receiving and counting the sharps than an embodiment without such magnets, but, unfortunately, would make the device again relatively expensive.

Barratt, in U.S. Pat. No. 4,167,230, also discloses a disposable receiver comprised of tray and cover elements which are confined to nest in a closed position: note FIG. 4 in 4,167,230 having cover 114 with base 112 wherein the base 112 may be attached to strip magnets 40 (see FIGS. 1-3 of 4,167,230) to attrack the sharps, i.e., tray device 36 comprises a foamed sheet 38 with a plurality of strip magnets 40 adhered to the upper surface of the sheet. See col. 3, lines 47-53 and col. 4, lines 17-29. The magnets presumably would be discarded with the rest of the device.

U.S. Pat. No. 4,013,100 to Sandel discloses a hinged sterilizable container for magnetizable surgical instruments, having magnetic means which completely cover the interior portion of the case to retain any magnetizable instruments placed within the case. Specifically, Sandel 4,013,100 uses magnet means 120 covering lower portion 14 of case 10 by an adhesive to collect ferrous-containing materials. Again, the magnets would not be resuable.

U.S. Pat. Nos. 3,727,658 (see FIGS. 1, 3 and 4 hereto) and 3,944,069 to Eldridge, Jr. (see FIG. 2 hereto), each disclose a disposable receiver for surgical implements comprising a pair of foldably connected pads which employ a plurality of magnetic bars to attempt to retain the sharps. However, we found that it is easy when using the 3,727,658 and 3,944,069 devices to have the sharps extend beyond the periphery of the device, which extension would present a hazard to operating room personnel, or worse yet, could cause the loss of the sharps in the operating room when the device is folded just prior to disposal. Moreover, FIG. 1 of the 3,727,658 also reveals by instrument 5 another problem: if an instrument is bound to two magnets 37 N" and "S" on each side of the hinge, it is likely to be lost from the device entirely when the device is folded. Again, the magnets of these devices are lost when the device is discarded.

U.S. Pat. No. 3,861,521 to Burtz discloses yet another disposable suture containing and needle organizer having pockets 11–15 or 21–28, and magnets 25. Again, the magnets would have to be discarded with the device upon disposal of the latter.

Perhaps less pertinent in Huck et al., U.S. Pat. 4,182,448, disclosing a receiver for disposing of used surgical sharps, particularly needles and needle blades, comprising an adhesive-coated 18, rectangular backing panel 11 having a cover panel 14 and two matrix panels 12 and 13 attached along the sides thereof. No magnet is employed. U.S. Pat. No. 4,116,333 to Pavel discloses a dispenser for sewing machine needles (in a non-analogous art, infra) employing a collecting means and cover means. U.S. Pat. No. 4,105,115 to Horvath et al. discloses a holder for retaining sutures, needles and other surgical products used during surgical operations, with one form of the holder being made from sheet material and having intermediate portions folded over adjacent intermediate portions thereof to form a plurality of V-shaped pockets which are adapted to receive and to retain the sutures and needles. Again, no magnets are utilized. U.S. Pat. No. 4,076,882 to Fenster et al. discloses foldable disposable pads having a layer of polyurethane on a layer of cardboard, part of the polyurethane foam having a pressure sensitive adhesive thereon. No magnets are involved. Presumably, the device would be utilized in the manner of Eldridge 3,727,658 and 3,944,069 above. Freitag, in U.S. Pat. No. 4,008,802 (see FIG. 6) teaches the manufacture of a pad of resilient material through which needles can be inserted, the pad provided with consecutively numbered needle receiving zones formed by ridges upstanding from an upper face of the pad, and by transversely extending lines across the ridges. This is similar in some respects to Erickson, U.S. Pat. No. 3,819,039, which teaches the manufacture of resilient material having a series of parallel slits defining abutments which bear against surgical sutures positioned in the slits to hold them securely and conveniently in place. Kovalcik et al., in U.S. Pat. No. 3,697,223, shows an autoclave tray for holding instruments wherein the instruments are placed on form-fitting intermediate trays in the container.

3. Structures in Non-Analogous, Remotely Analogous, and Obsolete Arts

British Pat. No. 294,298 to Cecil Beckwith Cave-Browne-Cave is directed to a container for fishing flies, which we consider to be in a non-analogous field. The patent discloses a container having an inserted magnetic bare means B and B' for holding magnetic articles attached to collecting means A in tight fitting engagement with base means B, B', with cover means A' capable of tight fitting engagement with the bare means A. The patent also discloses at page 1, lines 32–34, the use of an intermediate plate between the magnetic means and the item to be held (". . . or through an intervening layer of non-magnetic material such as celluloid, aluminum or the like . . . ").

French Pat. No. 1,216,548 to Eymard also discloses a container with magnetic means 12 and 13, an intermediate plate 1, a base means 15 and a cover means 16. Note also French Pat. No. 1,348,460 to Demets and Austrian Pat. No. 132,127.

The following are listed to show various aspects of preferred embodiments of the present invention which have appeared before in remotely analogous, non-analogous, and obsolete arts. Although some of the older patents are not directed to containers having a magnetic means, the patents do show material and external features in common with the container of the instant invention.

Kunik et al., in U.S. Pat. No. 3,982,631 disclose a dispenser container for magnetic needles employing magnet means 37 to retain needles, with the cover 29, 31, 32 and base means 22, 23, 24 and 26 adapted to fit in sealing engagement (see FIG. 2). Note also hinge 63 in FIG. 9 of the 3,982,631 patent. See also magnet 31 in LaBorde, U.S. Pat. No. 2,888,136.

Borst, U.S. Pat. No. 300,441 discloses a container with a cover means and base means connected by a hinge, having an intermediate compartment. Meinecke, U.S. Pat. No. 963,454, shows a container having a replacable collecting means that is designed to form fit with the base means. Underwood, U.S. Pat. No. 1,231,674 discloses a box similar to Borst, in having the cover means and base means connected by a hinge. The collecting means 5 formfits with the cover means. Kurtz, Jr., in U.S. Pat. No. 1,835,408 describes a container for holding razor blades. An intermediate layer 4 is attached by a hinge to both the upper and lower frame members. Warren et al. in U.S. Pat. No. 1,436,617 depict a container having a removable intermediate means 15. MacGregor, in U.S. Pat. No. 1,980,141, depicts a case for carrying syringe outfits having an intermediate collecting means that form fits with the base means. Collie, in U.S. Pat. No. 3,565,281, in a clearly non-analogous art, shows a container wherein the upper means is designed to fit tightly with a lower base means.

Just as remote are U.S. Pat. Nos. 59,095; 1,654,554; 2,176,452; 2,583,043; 2,588,589; 2,692,676; 3,248,167; 3,388,790 and 3,481,462. The 3,481,462, 3,388,790, 3,248,167, 2,692,676, 2,588,589, 2,583,043 and 2,176,452 are directed to disposable dental burr or surgical instrument holders/counters wherein magnets are not generally employed (but c.f. U.S. Pat. No. 3,248,167 at col. 1, lines 39–55). These patents seem to comprise a predecessor art to the instant field. U.S. Pat. Nos. 59,095 and 1,654,554 to Totten and Pasch are directed to containers in old and obsolete arts, respectively, for confining ferrous-containing materials.

Ger. Pat. Off. No. 26,51,315 discloses a packing procedure for needle type magnetic metal parts in which a magnetic field is produced in a non-magnetic package container. Of even less pertinence are Brit. Pat. Nos. 1,448,543, 1,514,390, Ger. Pat. Offenlegungsschriften Nos. 25,07,976; 26,57,627; 28,00,579; 26,09,228; 27,40,335; and 28,36,962; Ger. Pat. Auslegeschrift No. 26,01,512; and U.S.S.R. Pat. No. 365,203.

4. The Problem

A need has arisen over the last decade in the industry for a device to effect the counting and safe disposal of sharps in a quick fashion while at the same time performing the task in a very economical fashion. In the past, those skilled in the art have been placed in a position of either using expensive magnets in their disposable devices (and even then, in some instances, being faced with the risks of sharps dangerously protruding, which could prick hospital personnel, or sharps being lost from the prior art devices), only to discard same, or foregoing the use of magnets to accept increased risks of loss of control of the sharps or the use of strips of resilient material that are time-consuming for hospital personnel to employ.

We have found that hospital personnel who now are, by necessity, cost conscious, object to wasting the magnets and pads because of the expense of the magnets. These personnel have, on occasion, tried to throw away the surgical blades and needles and retain the pad and magnets, but have concluded that this approach should not be employed because of the risk of cutting themselves on dirty or infected needles or blades. The preferred state-of-the-art "magnet pad system" costs hospitals anywhere from 75¢-$1.20 (1980 dollars). A 400 bed hospital generally can perform 11,000 operations a year, so that it purchases $8,000-$11,000 of these items per year (1980 dollars), so that these expenses are not insignificant.

5. An Invention

After reviewing the preferred state of th art "magnet pad system" and discussing the problems presented by hospital personnel and observing activities of an operating room suite, we collectively arrived at a novel concept that in one preferred embodiment would have at least the following benefits over the prior art (the broadest concept of the invention and technical advance over the art involves less than the following):

(a) substantially lower costs;
(b) re-use of magnetic members (part of a base means);
(c) (preferred) visibility through lid of closed container;
(d) greater security; and
(e) closed storage.

The novel concept comprises separting the magnetic source from a collecting means into which the needles and magnets are placed. During the time of loading, the base means and collecting means are in tight-fitting engagement. After the loading of the collecting means, cover means (preferably transparent) are fastened to the collecting means. If the cover means and collecting means are transparent, the sharps can be counted both before and after the cover means is affixed. Most importantly, when it is desired, the closed container (cover means locked to the collecting means) with a reasonable pull can be separated from the base means, and together with the sharps, discarded.

SUMMARY OF THE INVENTION

The present invention advances the art by providing a reusable sterilizable secure base means containing a source of magnetism to be used in the operating room, together with (preferably transparent and disposable) inexpensive collecting means and cover means, which collecting means are in tight fitting with the base means so as to prevent sharps from dangerously protruding from the device, or being dislodged entirely. Our container for storing sharps, e.g., surgical needles or blades, comprises:

(a) base means formed of a reusable and sterilizable material and containing a source of magnetism;

(b) collecting means for surgical needles or blades, said collecting means shaped to provide an interlocking fit with said base means; and (c) cover means with said collecting means to form an enclosure, said cover means capable of tight-fitting engagement with and placement over said collecting means to prevent said surgical needle or blades from escaping from said enclosure when said cover means are in tight-fitting engagement with said collecting means, said collecting means and said cover means attached to each other by hinge means, said collecting means being provided with locking means to lock said cover means with said collecting means when said cover means is in tight-fitting engagement with said collecting means.

Preferably, at least the cover means of our device are transparent; most preferably, the cover means, collecting means, hinge means and lock means are transparent, and are continuous and made from one thermoformed, vacuum-molded or injection molded piece of plastic, such as polyvinyl chloride, polyvinyl acetate, polystyrene polyethylene terephthalate, or (most preferably) PETRA ® AW copolymer (Allied Chemical Co., Moristown, N.J.). We also prefer to manufacture the hinge means to have a sufficiently low modulus of elasticity and a sufficiently low section modulus to provide the hinge with a resulting low resiliency so that the cover means will only form an enclosure with the collecting means when the locking means is locked. Most preferably, we manufacture the hinge to have a modulus of elasticity and section modulus that are sufficiently low so that when the locking means are unlocked, an angle is formed between the axis of the cover means and the axis of the collecting means of at least about 180°.

The base means must be able to withstand temperatures capable of giving it repeated sterilization, and preferably must withstand temperatures of from about 270° F. to about 300° F. (i.e., in a saturated steam environment). While the magnetic source may comprise at least one metal or ceramic magnetic bar (three of four are better), we have found that when the source comprises several bars of barium ferrite filled polymer (such as nylon, or even more preferably, polypropylene sulfide), the source of magnetism can be manufactured inexpensively and with great control as it is induced by an electrical field that can be controlled. We desire the source of magnetism to be in a quantity sufficient to engage all surgical needles or blades in a predetermined proximity to the base means—preferably just sufficient to engage all surgical needles or blades placed within said collecting means (if the source of magnetism is too great, it may induce magnetism in instruments outside the immediate area of the base means). In our most preferred embodiment, we prefer the entire base means to be constructed as a uniform, continuous piece of barium ferrite filled polymer, further comprising one or more rib means, each engaging platform means of a predetermined configuration (preferably rectangular), each rib means containing a source of magnetism (e.g., having magnetism induced in it by an electrical field), and each rib means partially or entirely traversing the platform means, and each protruding the surface of the platform means. We prefer to utilize three or four ribs, that each comprise parallelopipeds, and most preferably, each have rectangular cross-sections.

In the most preferred embodiment of our invention, our novel container comprises:

(a) collecting means further comprising bottom tray means having a bottom wall, with apertures to fit in tightfitting engagement with the ribs of said base means, with side walls extending upwardly from said bottom wall and a flange extending outwardly around the upper periphery of said side walls to form a first vessel having a predetermined volumn;

(b) cover means further comprising a top tray means having a bottom wall with said side walls extending upwardly from said bottom wall and a flange extending outwardly around the upper periphery of said side walls, to form a second vessel having a predetermined volumn;

(c) the cover means and collecting means so dimensioned that when they are closed and locked, they form a nested configuration having an interference fit on at least one of the engageable side walls of the bottom tray means and top tray means; and (d) collecting means when locked with the cover means providing a predetermined distance between the rib means of the base means and the bottom wall of said cover means so as to securely encase surgical needles or blades between the rib means and the bottom wall of the cover means.

The interference fit is suitably provided by lock means comprising the engaging side walls opposite the hinge means, wherein said engagable side walls are substantially parallel and form an acute or obtuse angle with the bottom wall of the collecting means when the collecting means and cover means are locked, so that the cover means "snaps" into the collecting means forming the enclosure. Tab and aperture means formed into each of the pair of adjoining flanges of the collecting means and cover means extending outwardly from one side of the engagable side walls (also preferably opposite the hinge means) of the bottom tray means and top tray means are suitable as a device to effect opening and closing the cover means and collecting means.

The use of two or more parallel magnetized ribs mounted on and protruding from a platform which exists in tight-fitting engagement with conforming apertures in the collecting means synergistically (1) provide a source of magnetism just adequate to attract all sharps when placed into the container and (2) secure the sharps between collecting means and cover means when the locking means is locked.

BRIEF DESCRIPTION OF THE DRAWINGS

FIGS. 1-6 depict some of the devices representative of the prior art that we have obtained:

FIGS. 7-10 depict devices comprising some preferred embodiments of the invention as described also in Examples 1-4, respectively.

DETAILED DESCRIPTION OF THE PREFERRED EMBODIMENTS

As a preferred alternative to metal and ceramic bars employed as ribs for use in the base means, we prefer a barium-ferrite filled polymer, such as nylon or polypropylene sulfide. Most preferably, the entire base means, including the ribs, is one continuous piece of barium ferrite filled polypropylene sulfide, such as a continuous molded piece of RYTON ® (Phillips 66 Petroleum Co., Oklahoma City, Okla.) polymer having the barium ferrite dispersed throughout the polymer. See FIG. 10. Using such a molded polymer having a barium ferrite dispersion, it is possible to induce a predetermined strength of magnetism along the surface of the ribs just enough to attract all sharps placed within the collecting means but not sufficient to induce any residual magnetism in any ferro-magnetic medical instruments in the area immediately surrounding the novel device. Note U.S. Pat. No. 3,727,658, col. 2, lines 60–67, and col. 3, lines 1–7 thereof incorporated herein; note also U.S. Pat. No. 4,013,109, col. 3, lines 4–12 thereof, incorporated herein. The Xolox Corporation (6932 Gettysbury Pike, Fort Wayne, Ind. 46804) is experienced in inducing magnetism by an electric field in barium ferrite-filled polypropylene sulfide, and controlling the strength and direction of the poles of the induced magnetic field. See Example 4, infra. The barium nitrite-filled polypropylene sulfide can also be resterilized at least about 1000 times at 270° F. to about 300° F. under conditions of steam sterilization, or, in the alternative, can be repeatedly sterilized by ethylene oxide procedures in a sterilizer as known by those skilled in the art. Radiation techniques such as those used by the Radiation Technology Corp. in Danville, N.J., using from about 1.0 to perhaps as much as about 2.5 Megarads sufficient to insure a $10^{-6}$ probability that any organisms exist could also be used. It is also desired that three or four ribs having adjacent opposite polarity from side to side on each rib, e.g., #1: N-S; #2: S-N; #3 N-S, etc., polarity in sequence. Ribs of 0.5 inch width and about 0.1875 to about 0.250 inch depth are sufficient.

As mentioned, the collecting means, hinge means, lock means and cover means (container) are all preferably made of a continuous piece of polymer, such as polyvinyl acetate, polystyrene, polyethylene terephthalate (PETG, such as that made by the Eastman Kodak Chemical Co., Rochester, N.Y.), and most preferably, PETRA ® AW (Allied Chemical Co., Morristown, N.J.). The polymer is preferably thermoformed. We prefer radiation sterilization to sterilize our containers. Any thermoformable polymer capable of (1) gamma ray sterilization at the recited 1.0–2.5 Megarad strength, or (2) sterilization by any known technique, is acceptable.

Dimensions and tolerances in the manufacture of the novel container are important. We prefer from about 0.010 inch to no more than about 0.015 thickness for the collecting means and cover means; a thickness that is too thin (e.g., generally less than 0.005 inch) causes the device to lose rigidity; a thickness too great makes the container unnecessarily expensive. The depth of the collecting means apertures and the depth of the ribs in the base means are enough to provide the novel container means be secure when in tight-fitting engagement with the base means, and are preferably each about 3/16 inch to about ¼ inch. When the container is closed, i.e., the lock means joining the cover means with the container means is locked, a gap of about 0.003 inch is preferred between the cover means and the top of the apertures in the container means, so that, upon closing, the sharps are secured. A number of companies and individuals well skilled in the thermoforming art are available to manufacture plastic pieces having such tolerances, e.g., SLM Manufacturing Corp. of Somerset, N.J.; FMC Corp., Packaging Machinery Div., Horsham, Pa., and Adam Savino, 28 Dwight Place, Fairfield, N.J. 07066.

As indicated above, for opening and closing the device, we prefer to employ tab and aperture means formed into each of the pair of adjoining flanges of the collecting means and cover means extending outwardly from one side of the engageable side walls of the bottom tray of the collecting means and the top tray of the cover means. Of course, other alternatives are possible, such as employing notches and cooperating U-shaped slots in each of the flanges of the cover means and container means. See col. 4, lines 58–66 of U.S. Pat. No. 4,193,496, incorporated herein. Still another alternative is to employ a positive locking tab in the flange of the cover means cooperating with a receiving aperture in the flange of the container means, e.g., col. 4, line 66, to col. 5, line 2 of the 4,193,496 patent.

Still another embodiment in the bottom tray of the container means between the rising apertures that can be employed is a layer of resilient material (such as polyurethane or polystyrene foam) or adhesive that might help to secure sharps partially dislocated. The resilient material can take the form of rectangular strips adhering to the bottom tray of the container means by a pressure sensitive adhesive having narrow slots numbered at regular intervals. See U.S. Pat. Nos. 3,819,039 and 4,008,802, incorporated herein. A suitable pressure sensitive adhesive is any of the polyester films having a tacky styrene-butadiene rubber adhesive layer on each side.

As described, any kind of hinge can be employed joining the cover means to the collecting means (e.g., metal hinges, live hinges with spaces, e.g., U.S. Pat. Nos. 4,243,140 and 4,193,496; or by tape, e.g., U.S. Pat. No. 4,167,230), but we prefer a continuous, flexible, moldable piece of plastic which, while avoiding cracking, has little resiliency or memory in flexing, i.e., has a low modulus of elasticity and a low section modulus, most preferably so that the two planes of the cover means and container means can rest when the cover means is opened at close to about 180°.

Although our invention has been described above in terms of selected preferred embodiment, it should not be limited thereto, since other equivalent embodiments and modifications and improvements thereto will readily occur to one skilled in the art. It is, therefore, understood that the appended claims following the Examples cover all such equivalent embodiments and modifications, and improvements as fall within the spirit and scope of the invention.

EXAMPLE 1

Figures 1, 2, 3:
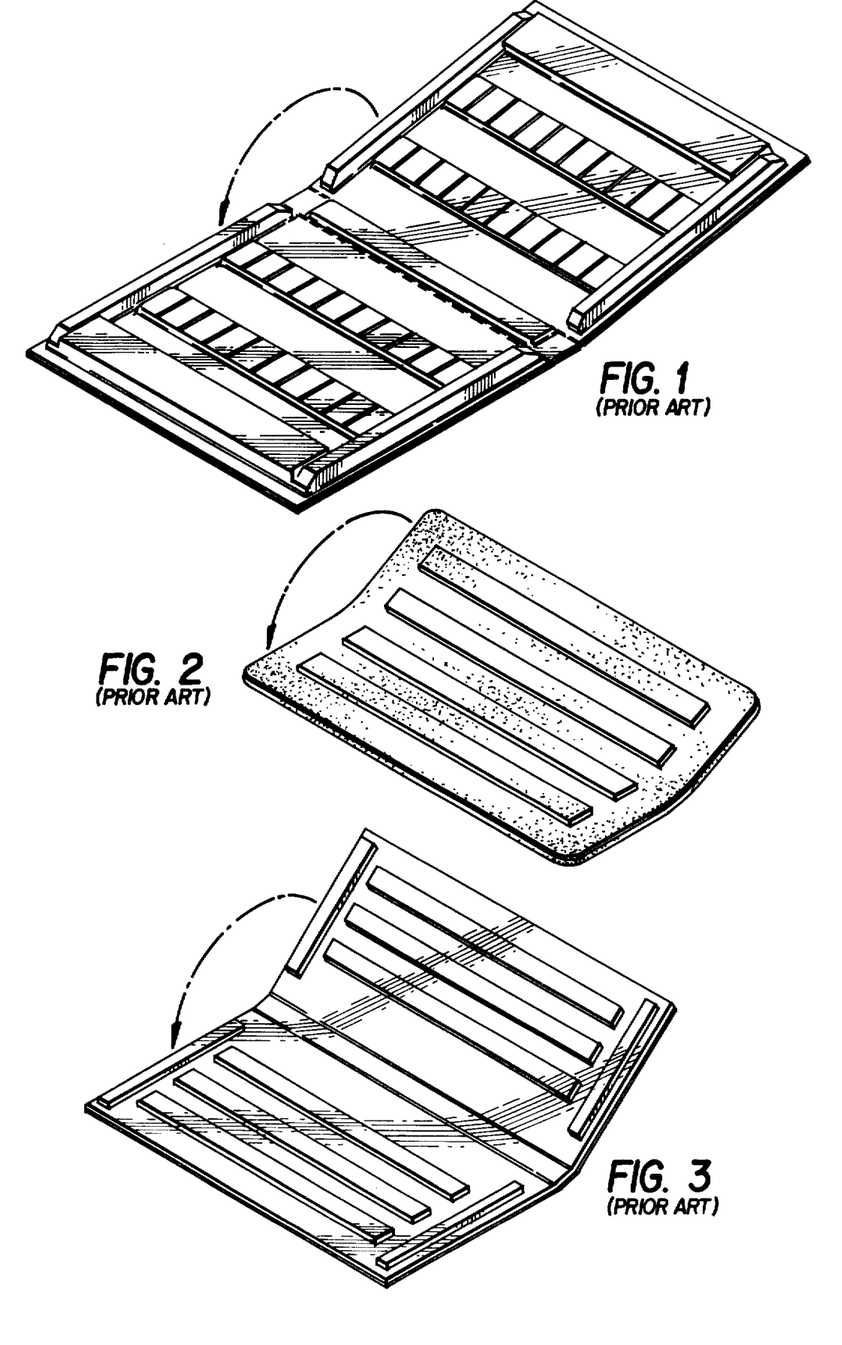
FIG. 1 is an end view of a 4"×8" (est.) prior art device as unfolded having 4 magnetic bars; it appears to be a commercial form of U.S. Pat. No. 3,727,658.
FIG. 2 is an end view of a similar 3"×4" (est.) prior art device as unfolded having 4 magnetic bars; it appears to be another commercial form of U.S. Pat. No. 3,727,658.
FIG. 3 is an end view of a layer 6"×4" (est.) prior art device as unfolded having 6 magnetic bars; the device is marked "DISPOSA-MAG (logo) TM M-6" by Instranetics, Inc. of Fullerton, Calif. 92631, and appears to be another commercial form of U.S. Pat. No. 3,727,658, except modified.
Figures 4, 5, 6:
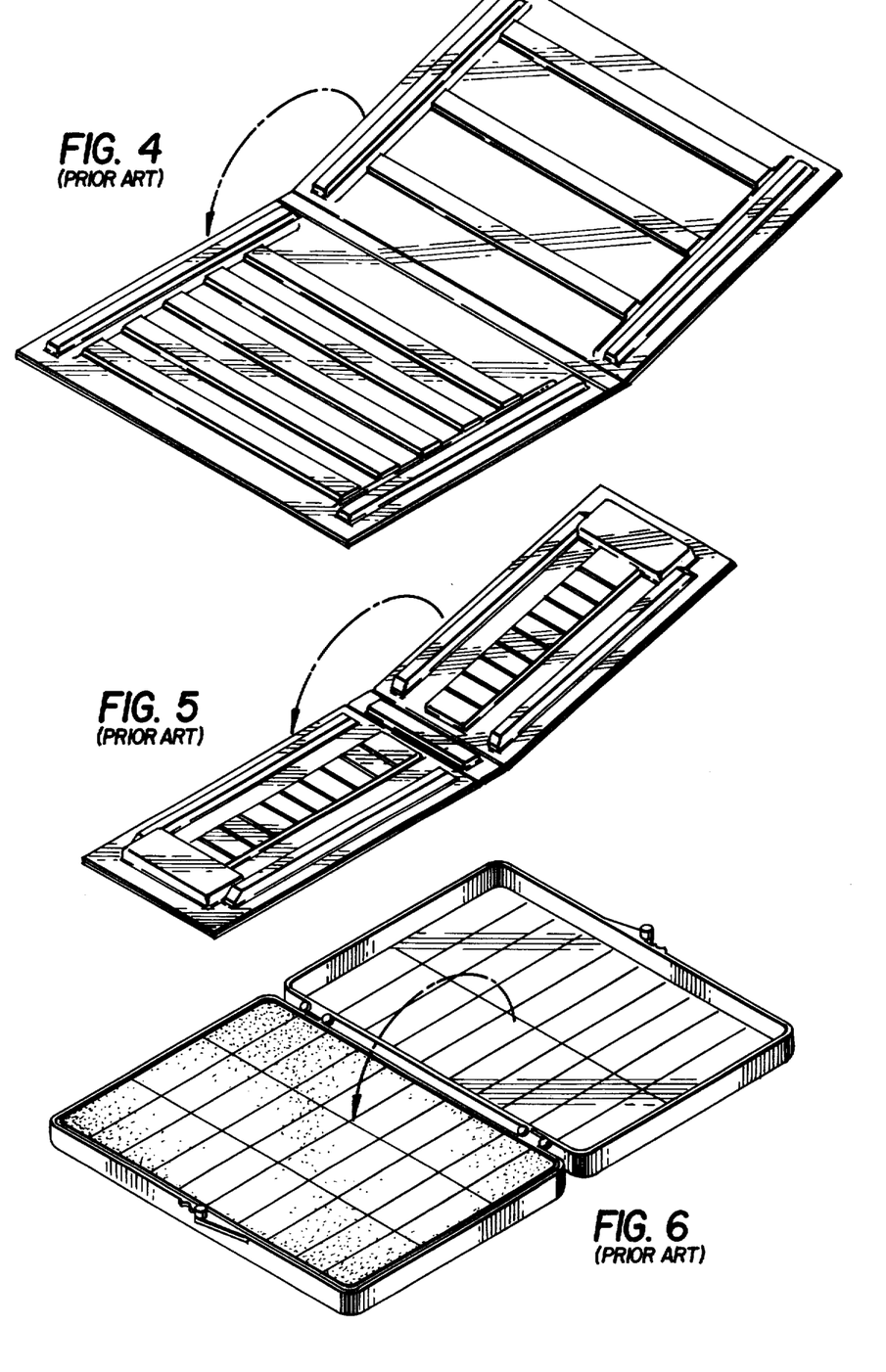
FIG. 4 is yet another end view of a still larger prior art 8"×5" (est.) device, as unfolded; the device is marked "DISPOSA-MAG (logo) TM M-8" by Instranetics, Inc., and appears to be yet another commercial form of U.S. Pat. No. 3,727,658, except modified.
FIG. 5 is an end view of a 2"×8" (est.) prior art device by Instranetics marked "DISPOSA-COUNT TM, 'Magnetic Sharps Count and Disposable System'".
FIG. 6 is an end view of a Bio-Metics (6576 Trinity Court, Dublin, Calif. 94566) "ACURA-COUNT TM II" foldably nested device having 50 positions and a foam backing; it seems to be a commercial embodiment modifying U.S. Pat. Nos. 4,008,802 and 4,193,496.
Figure 7:
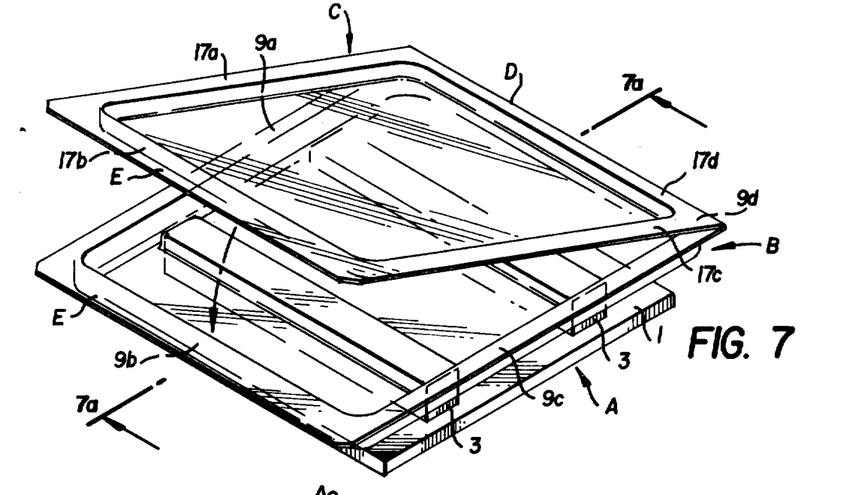
FIG. 7 is an end view of a 4"×4" base means utilizing two parallel metal magnets, in tight-fitting engagement with a one-piece disposable collecting and cover means.
Figure 7A:
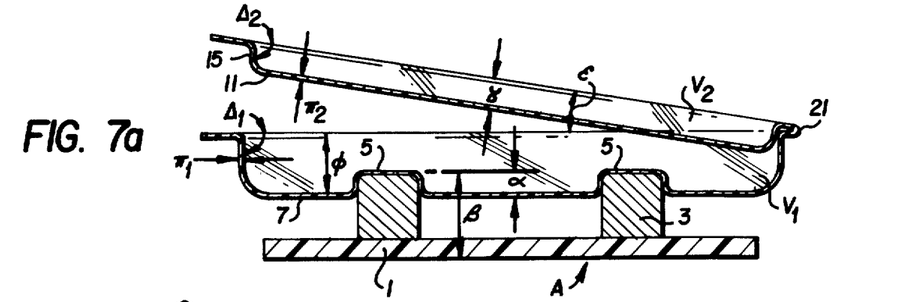
FIG. 7(a) is a cross-sectional view taken along line 7a—7a of FIG. 7.
Figures 7B, 8:
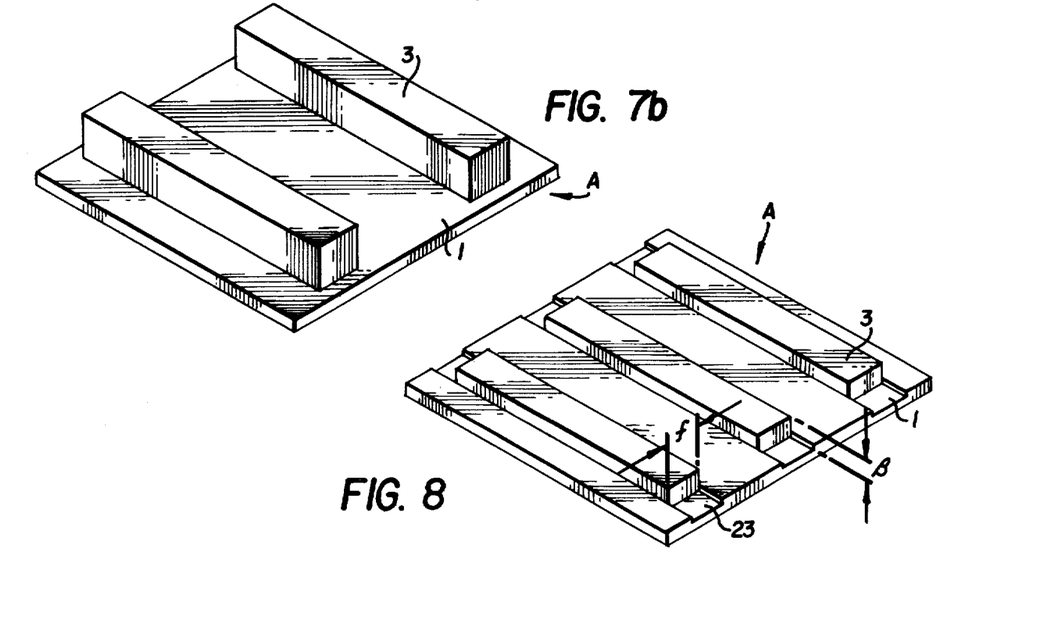
FIG. 7(b) is an end view of the 4"×4" base means of FIG. 7 in isolation.
FIG. 8 is an end view of a 4"×4" green base means utilizing three parallel metal magnets.

In this Example, reference is made to FIGS. 7, 7(a), and 7(b) hereto. Base means A comprises a 4"×4" platform 1, upon which are located two metal magnets, each ⅛"×178"×4", which are secured to the platform by a suitable adhesive. The magnets are adapted to engage collecting means B in tight-fitting engagement; collecting means B comprises a bottom tray 7 having two abutments 5, each designed to engage the ribs 3 base means A in tight-fitting engagement. The abutments 5 have a uniform depth $\alpha$, which, while equal to or less than the cross-sectional depth $\beta$ of the ribs 3, are sufficient to secure the novel container means (i.e., collecting means B, hinge means D, locking means E and cover means C) to the base means so that the container means will not be easily jarred loose in the operating room. Platform 1 can either be secured to any conforming surface in the operating room, e.g., a tray, portable table, etc., or be of sufficient weight to retain stability.

Collecting means B has a predetermined volumn $V_1$ more than the volume $V_2$ of cover means C. The collecting means has four side walls of equal depth $\phi$ with tray 7 extending upwards; flanges 9a–9d extend outwardly at the upper edge of each of the side walls 13, respectfully. Cover means C is secured to the collecting means B via hinge means D; here hinge means D comprises a piece of plastic 21 continuous with the collecting means B and cover means C and having a modulus of elasticity and section modulus sufficiently low so that when the locking means E is unlocked, an angle $\epsilon$ is formed between the axis of the cover means and the axis of the collecting means of at least 180°.

The cover means C has bottom tray wall 11 with four side walls 15 of equal depth $\gamma$. Cover means C, hinge means D, and collecting means B are made of one continuous piece of PETRA ® AW plastic, wherein the cover means C and collecting means B are of thicknesses $\pi_2$ and $\pi_1$, respectively. Side walls 15 of the cover means C engage flanges 17a–17d, which, when the container means is closed, are parallel to flanges 9a–9d, respectfully. The distances $\pi_1$, $\pi_2$, $\alpha$, $\phi$, and $\gamma$ are selected so that the distance $(\phi+\pi_2)-(\gamma+\alpha+\pi_1)$ represents a predetermined distance or clearance between the ribs 3 of the base means A and the bottom wall 11 of the cover means C when the container means is closed so as to securely encase sharps between the ribs 3 and the top wall 11. This predetermined clearance is preferably about 0.003". Preferably, each of flanges 9a, 9c and 9d and 17a, 17c and 17d are of equal width and from about 1/16" to about ⅛"; their purpose is to provide structural rigidity to the container means. Locking flanges 9b, 17b are preferably wider, of about ¼"–½". Thicknesses $\pi_1$ and $\pi_2$ are preferably each of about 0.010"–0.015".

Locking means E comprises only the use of side walls 13 and 15 of the collecting means and cover means, respectfully, opposite the hinge means D. The side walls are so constructed as to be parallel and in very tight-fitting engagement when the cover means C is inserted into the collecting means B. Preferably, these side walls 13 and 15 have angles $\Delta_1=\Delta_2<90°$, so that the side walls snap shut when the locking means is locked (not shown). In the alternative, $\Delta_1=\Delta_2>90°$.

EXAMPLE 2

FIG. 8 depicts from an end view a 4"×4" green plastic base 1 having three metal magnets 3 of width f=½" and depth $\beta$=¼". The base means is constructed so that the magnets 3 fit into slots 23 of width f and are secured by an adhesive.

EXAMPLE 3

Figures 9, 10:
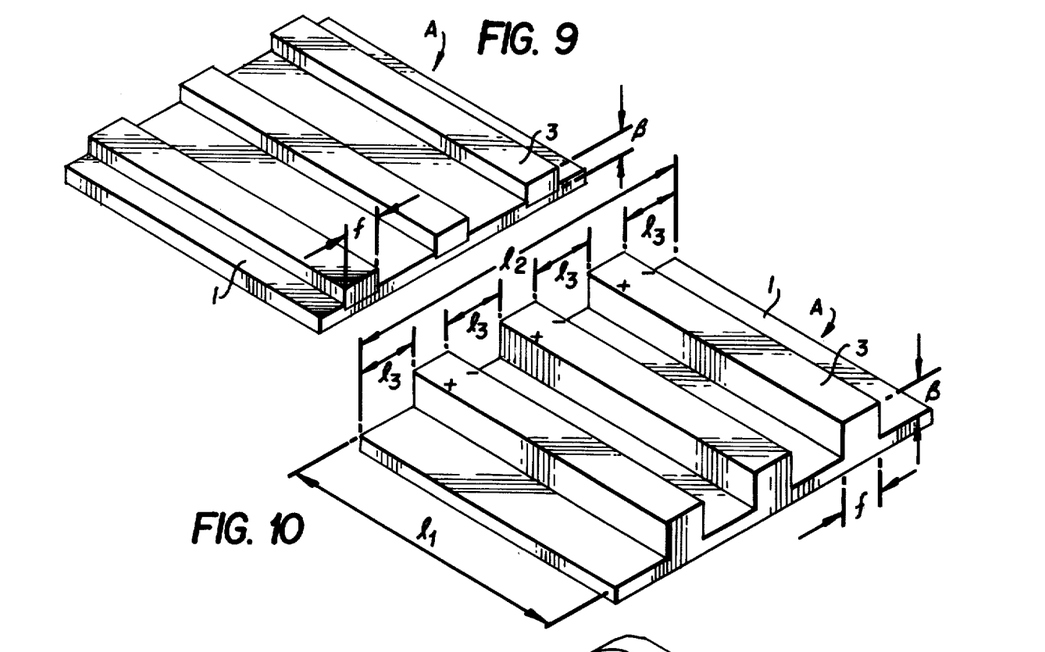
FIG. 9 is an end view of a 3"×3" gray base means having three parallel metal magnets.
FIG. 10 is an end view of a 4½"×4" much preferred base means comprising a one-piece continuous material of uniform barium-ferrite filled polypropylene sulfide, which base means includes three protruding parallel ribs or bars, of which magnetism has been induced by an electrical field.

FIG. 9 depicts from an end view a 3"×3" gray metal base 1 with three magnets 3 of width f=½" and depth $\beta$=¼", except that the magnets 3 traverse the entire length of the base 1, which is preferred.

EXAMPLE 4

Figures 10A, 10B:
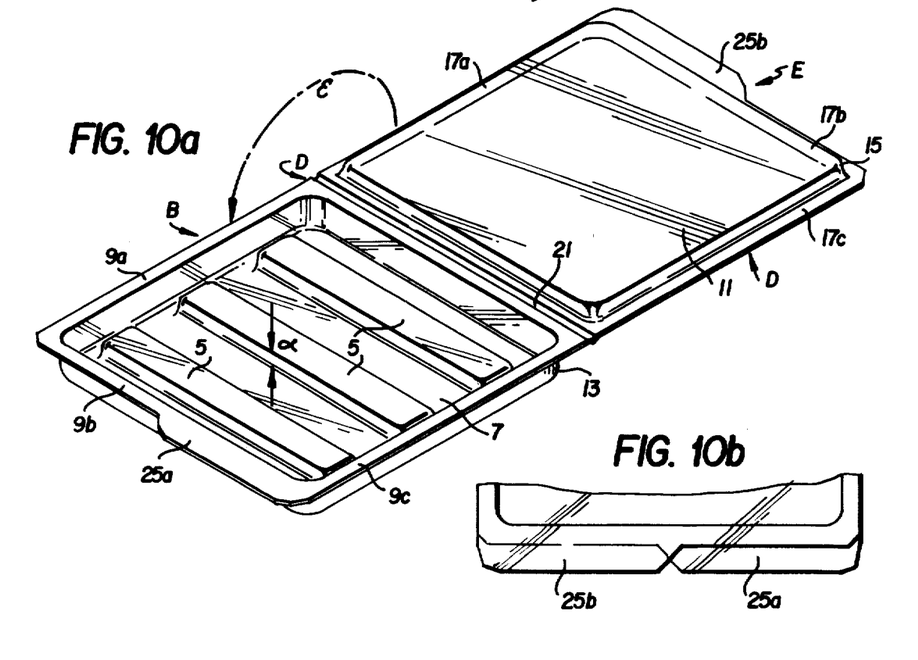
FIG. 10(a) is an end view of a one-piece disposable collecting and cover means, which collecting means may be employed in tight-fitting engagement with the base means of FIG. 10.
FIG. 10(b) is a perspective view taken from the vertical along line 10b–10d of FIG. 10(a) showing the tabbed locking means of the one-piece disposable collecting and cover means.
Figure 11:
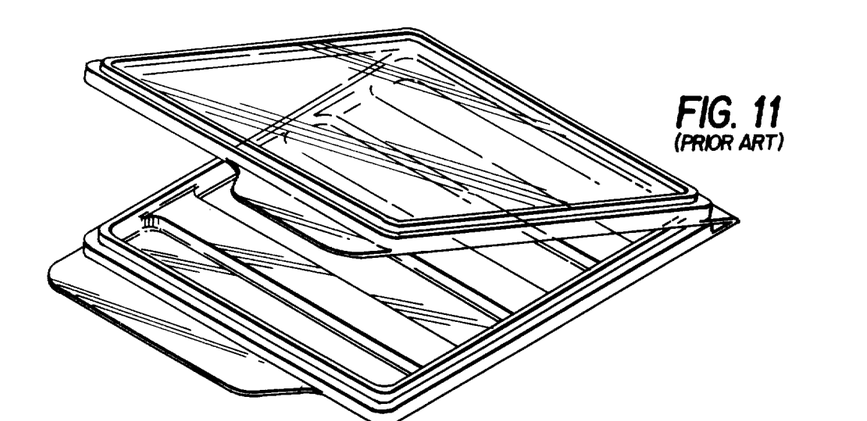
FIGS. 11-15 also show various configurations of the prior art.
Figures 12, 13, 14:
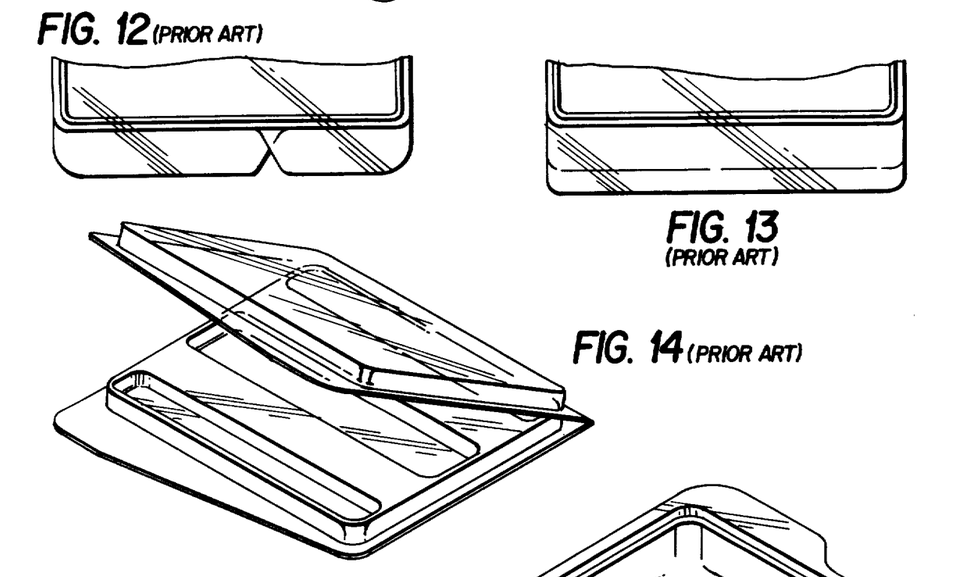
Figure 15:
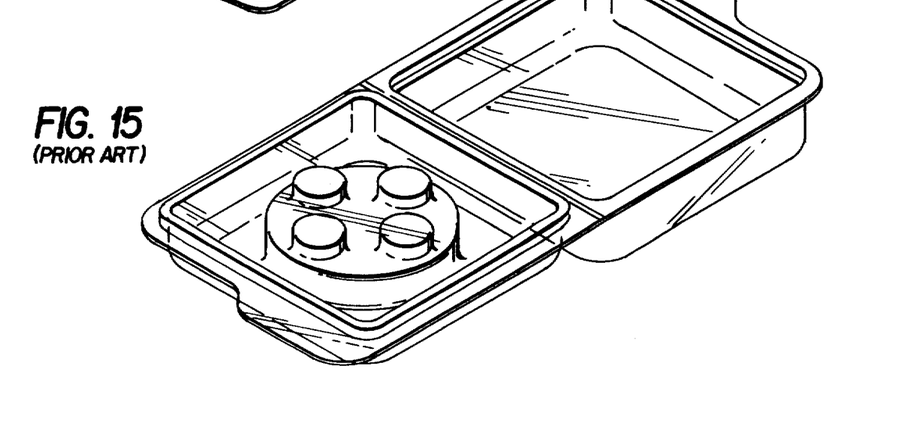

FIGS. 10, 10a and 10b illustrate a most preferred embodiment of our invention. The base means A of FIG. 10 comprises a single molded piece of barium ferrite-filled RYTON ® (Phillips 66 Petroleum Co., Oklahoma City, Oklahoma) polypropylene sulfide of length $l_2$=4.5" and width $l_1$=4.0", having magnets of width f=½" equally spaced ¾" from the edges and from each other. The ribs 3 are of depth $\beta$=¼", and have magnetism induced by an electrical field. The base means is manufactured for us by the Xolox Corporation, 6932 Gettysburg Pike, Fort Wayne, Indiana 46804. This base means A can withstand about 1000 steam (saturated) autoclave cycles at 270° F.–300° F. without demagnetizing or losing its size, shape or structural integrity; it will not induce residual magnetism to any ferromagnetic medical instruments when these come into contact with the magnets outside a 0.005" gap.

Collecting means B and cover means C are similar to that of Example 1, except that when open, the hinge is so constructed that it lies flat when open, i.e., angle E is 180°. The cover means C and collecting means B, together with hinge means D, (21) and locking means E are made of a continuous piece of thermoformed PETRA ® AW plastic of thickness $\pi_1$,=$\pi_2$=0.010". (Adam Savino, 28 Dwight Place, Fairfield, N.J. 07006). Flanges 9a–9d and 17a–17d are of width ⅛", except that flanges 9b and 17b are provided with tabs 25a and 25b, respectfully, extending an extra ¼". Locking means is provided by having the side walls 13 and 15 adjacent the tabs 25a and 25b constructed at angles $\Delta_1=\Delta_2\approx110°$, (not shown), so that the cover means C snaps into the collecting means B when the locking means E is locked, i.e., by interference fit. The cover means C and collecting means B are of such dimensions and have volumns $V_2$ and $V_1$, respectfully, that they fit in a nested configuration when closed. The locking means E is opened when the tabs 25b and 25a are forced apart.

The bottom tray 7 of the collecting means B has apertures 5 adapted to tight-fit ribs 3 of the base means A; the ribs 3 and apertures 5 are so constructed that the depth f of the apertures equals the width b of the ribs and the bottom tray rests flush against platform 1 of the base means A. Clearance $(\phi+\pi_2)-(\gamma+\alpha+\pi_1)$ is so constructed to be about 0.003".

We claim as our invention:

1. A container for storing sharps, comprising:
   (a) base means formed of a reuseable and sterilizable material, said base means having a platform and at least one rib of magnetic material fixed to said platform and projecting upwardly from said platform to engage collecting means;
   (b) collecting means for surgical needles or blades, said collecting means having at least one inverted recess to engage said at least one rib of said base means, said at least one inverted recess and at least one rib dimensioned in such a way to provide a reversibly interlocking frictional fit between said collecting means and said base means so as to make said collecting means disposable by removing said from said base means; and
   (c) cover means with said collecting means to form an enclosure, said cover means capable of tight-fitting engagement with and placement over said collecting means to prevent said sharps from escaping from said enclosure when said cover means are in tight-fitting engagement with said collecting means, said collecting means and said cover means attached to each other by hinge means, said collecting means being provided with locking means to lock said cover means with said collecting means when said cover means is in tight-fitting engagement with said collecting means.

2. The container of claim 1, wherein said cover means are transparent.

3. The container of claim 1, wherein said at least one rib comprises a metal or ceramic magnetic bar.

4. The container of claim 3, wherein said bar traverses said base means.

5. The container of claim 1, wherein said collecting means and said cover means are transparent and disposable.

6. The container of claim 1 or claim 3, wherein said at least one rib is present in a quantity sufficient to engage all surgical needles or blades in a predetermined proximity to said base means.

7. The container of claim 6, wherein said at least one rib is present in a quantity sufficient to engage all surgical needles or blades placed within said collecting means.

8. The container of claim 1, wherein said collecting means, hinge means, cover means and locking means comprise a continuous, transparent piece of plastic.

9. The container of claim 1, wherin said base means can withstand repeated sterilization at temperatures of from about 270° F. to about 300° F.

10. The container of claim 1, wherein said at least one rib of said base means comprises barium ferrite filled nylon, wherein magnetism is induced by an electrical field.

11. The container of claim 1, wherein said at least one rib of said base means comprises barium ferrite filled polypropylene sulfide, wherein magnetism is induced by an electrical field.

12. The container of claim 10 or claim 11, wherein the entire base means, comprises a continuous piece of barium ferrite filled polymer.

13. The container of claim 1 having two or more ribs, wherein the surface of said platform is rectangular and consists of substantially a two-dimensional plane, and a cross-section taken along any axis of each rib protruding from said surfaces is parallelopiped.

14. The container of claim 13, wherein the ribs are of equal dimensions and any two adjacent ribs are located at predetermined and uniform intervals from each other.

15. The container of claim 8, wherein said hinge means has a sufficiently low modulus of elasticity and a sufficiently low section modulus to provide said hinge with a low resiliency so that the cover means will not form an enclosure with the collecting means when the locking means is unlocked.

16. The container of claim 15, wherein the modulus of elasticity and section modulus are each sufficiently low so that when the locking means are unlocked, an angle is formed between the axis of the cover means and the axis of the collecting means of at least about 180°.

17. The container of claim 8, wherein said continuous, transparent piece of plastic is thermoformed, vacuum molded, or injection molded, and comprises one or more polymers selected from the group consisting of PETRA ®, polyvinyl chloride, polyvinyl acetate, polystyrene, and polyethylene terephthalate copoylmer.

18. The container of claim 1, wherein:
(a) said collecting means further comprises bottom tray means having a bottom wall, with recesses to fit in tight-fitting engagement with the ribs of said base means, with side walls extending upwardly from said bottom wall and a flange extending outwardly around the upper periphery of said side walls to form a first vessel having a predetermined volumn;
(b) said cover means further comprises top tray means having a bottom wall with side walls extending upwardly from said bottom wall and a flange extending outwardly around the upper periphery of said side walls, to form a second vessel having a predetermined volume;
(c) said cover means and collecting means so dimensioned that when they are closed and locked, they form a nested configuration having an interference fit on at least one of the engagable side walls of the bottom tray means and top tray means;
(d) said collecting means, when locked with said cover means providing a predetermined distance between the rib means of the base means and the bottom wall of said cover means so as to securely encase surgical needles or blades between said rib means and said bottom wall of said cover means.

19. The container of claim 18, wherein the interference fit is provided by lock means comprising the engaging side walls opposite the hinge means, wherein said engagable side walls are substantially parallel and form an acute or an obtuse angle with the bottom wall of the collecting means when the collecting means and cover means are locked.

20. The container of claim 18 or 19, further comprising tab and aperture means formed into each of the pair of adjoining flanges of the collecting means and cover means extending outwardly from one side of the engagable side walls of the bottom tray means and top tray means.

21. A container for storing sharps, comprising:
(a) base means formed of a reuseable and sterilizable material, said base means having a platform and at least one rib of magnetic material fixed to said platform and projecting upwardly from said platform to engage collecting means;
(b) collecting means for surgical needles or blades, said collecting means having at least one inverted recess to engage said at least one rib of said base means, said at least one inverted recess and at least one rib dimensioned in such a way to provide a reversibly interlocking frictional fit between said collecting means and said base means so as to make said collecting means disposable by removing same from said base means; and
(c) cover means with said collecting means to form an enclosure, said cover means capable of tight-fitting engagement with and placement over said collecting means to prevent said sharps from escaping from said enclosure when said cover means are in tight-fitting engagement with said collecting means, said collecting mans and said cover means attached to each other by hinge means, said cover means and said base means attached to each other by hinge means, said collecting means being provided with locking means to lock said cover means with said collecting means when said cover means is in tight-fitting engagement with said collecting means.

22. A container for storing sharps, comprising:
(a) base means formed of a reuseable and sterilizable material be, said base means having a platform and at least one rib of magnetic material fixed to said platform and projecting upward from said platform to engage collecting means;
(b) collecting means for surgical needles or blades, said collecting means having at least one inverted recess to recess and at least one rib of said base means, said at least one inverted recess and at least one rib dimensioned in such a way to provide a reversible interlocking frictional fit between said collecting means and said base means so to make said collecting means disposable by removing same from said base means; and
(c) cover means with said collecting means to form an enclosure, said cover means capable of tight-fitting engagement with and placement over said collecting means to prevent said sharps from escaping from said enclosure when said cover means are in tight-fitting engagement with said collecting means, said collecting means being provided with locking means to lock said cover means with said collecting means when said cover means is in tight-fitting engagement with said collecting means.

* * * * *